(12) United States Patent
Sollmann

(10) Patent No.: US 9,745,430 B2
(45) Date of Patent: Aug. 29, 2017

(54) ELASTIC MONOFILM AND METHOD OF MAKING A DISPOSABLE HYGIENE ARTICLE

(71) Applicant: MONDI Gronau GmbH, Gronau (DE)

(72) Inventor: Henner Sollmann, Gronau (DE)

(73) Assignee: MONDI GRONAU GMBH, Gronau (DE)

( * ) Notice: Subject to any disclaimer, the term of this patent is extended or adjusted under 35 U.S.C. 154(b) by 0 days.

(21) Appl. No.: 14/632,034

(22) Filed: Feb. 26, 2015

(65) Prior Publication Data
US 2016/0251487 A1 Sep. 1, 2016

(51) Int. Cl.
C08J 5/18 (2006.01)
A61L 15/42 (2006.01)
A61L 15/22 (2006.01)
C08L 53/02 (2006.01)

(52) U.S. Cl.
CPC ............... *C08J 5/18* (2013.01); *A61L 15/225* (2013.01); *A61L 15/42* (2013.01); *C08L 53/02* (2013.01); *C08J 2353/02* (2013.01); *C08J 2425/06* (2013.01)

(58) Field of Classification Search
CPC ................................ B32B 5/022; B29C 47/00
USPC ..................................... 156/244.11
See application file for complete search history.

(56) References Cited

U.S. PATENT DOCUMENTS

| | | | | |
|---|---|---|---|---|
| 5,164,436 A | * | 11/1992 | Maier | .................... C07C 67/26 524/277 |
| 8,492,480 B2 | | 7/2013 | Ooishi | |
| 2006/0139655 A1 | * | 6/2006 | Tixier | ................ G01B 11/0641 356/504 |
| 2011/0046307 A1 | * | 2/2011 | Takeshi | ...................... C08J 5/18 525/89 |
| 2013/0079471 A1 | * | 3/2013 | Brown | .................. C08F 297/04 525/241 |

* cited by examiner

*Primary Examiner* — Jeffrey Mullis
(74) *Attorney, Agent, or Firm* — Andrew Wilford

(57) ABSTRACT

The invention relates to an elastic monofilm having a film thickness between 20 µm and 100 µm, comprising an asymmetric styrene-diene triblock copolymer at a content between 35 wt % and 90 wt % as a first polymer substance A and comprising a second polymer substance B. According to the invention, polystyrene is provided at a content between 8 wt % and 40 wt % as the second polymer substance B.

5 Claims, 3 Drawing Sheets

ELASTIC MONOFILM AND METHOD OF MAKING A DISPOSABLE HYGIENE ARTICLE

FIELD OF THE INVENTION

The present invention relates to an elastic monofilm having a film thickness between 20 µm and 100 µm, comprising a percentage of an asymmetric styrene-diene triblock copolymer between 35 wt % and 90 wt % as a first polymer substance A and comprising a second polymer substance B.

BACKGROUND OF THE INVENTION

Elastic monofilms based on styrene block copolymers are frequently used in practice for elastic laminates from which elastic sections, such as diaper ears or elastic closure strips of diapers, in particular baby diapers, are formed.

For an elastic monofilm, it must be noted that the elastic monofilm, in particular when used on a disposable article, should be as thin as possible and therefore as economical as possible, while on the other hand must have sufficient load capacity and maximum tensile force.

Further conflicting requirements for such a monofilm are the requirement that, on the one hand, an elastic element formed from the monofilm should be evenly and, at the beginning of the elongation process, easily stretchable, while on the other hand the monofilm must have adequate tensile strength for the processing of the monofilm. In this way, excessive stretch or even tearing of the film must be prevented during handling.

The fact that, on the basis of a production direction of the film, the stretch behavior is different in the production direction (machine direction—MD) and perpendicular thereto in a transverse direction (CD), can be utilized to a certain extent. The monofilms are, in particular, processed into laminates and later into individual laminates in such a way that stretch occurs in the transverse direction (CD) in the finished product.

The known monofilms based on styrene block copolymers are frequently formed from symmetric triblock copolymers such as styrene-isoprene-styrene copolymer or styrene-butadiene-styrene copolymer.

An elastic monofilm of the type in question, comprising an asymmetric styrene-diene triblock copolymer at a content between 35 wt % and 90 wt % as a first polymer substance and comprising a second polymer substance, is known from EP 2 264 101 [U.S. Pat. No. 8,492,490]. The second polymer substance is also a styrene-diene triblock copolymer, that, however, has a symmetric or at least less asymmetric block structure.

Thus, the film is composed of styrene-diene triblock copolymer, wherein different triblock copolymers must be kept at hand and mixed with each other.

OBJECT OF THE INVENTION

Against this background, the problem to be addressed by the present invention is that of specifying an elastic monofilm that, while having the smallest possible thickness, is distinguished by a tensile strength in a manufacturing direction that is adequate for the processing and good elastic properties transversely thereto.

SUMMARY OF THE INVENTION

The subject matter of the invention and the solution to the problem are that, on the basis of an elastic monofilm having the features described above, polystyrene is provided at a content between 8 wt % and 40 wt %, especially preferably at a content between 10 wt % and 20 wt %, as the second polymer substance B.

Thus, according to the invention, an asymmetric styrene-diene triblock copolymer, preferably a styrene-isoprene-styrene block copolymer, is mixed with a simple polystyrene in order to form a film that has adequate tensile strength and stability in a manufacturing direction and good stretchability transversely thereto.

Accordingly, the elastic monofilm according to the invention has pronounced anisotropy, which is advantageous with regard to the processing of the monofilm and the use as an elastic layer of a laminate for disposable hygiene products. It is known that, in styrene-diene triblock copolymers, the styrene terminal blocks effect a certain stabilization, while the diene intermediate block enables elastic stretch. It is observed that, on a microscopic scale, a phase-separated structure can arise, with the result that a sort of grid or mesh having stiff and elastic regions is formed.

Against this background, EP 2 264 101 A1 describes that both symmetric styrene-diene triblock copolymers and asymmetric styrene-diene triblock copolymers can be used as constituents of a monofilm to change or set the elastic properties.

In the context of the invention, asymmetric refers to styrene-diene triblock copolymers whose terminal blocks have a mass ratio of between 2:1 and 5:1.

In the context of the invention, the content is at least 30 wt %. The styrene-diene triblock copolymer as polymer substance A is preferably the main constituent of the elastic film, so that polymer substance A is then contained in the monofilm at a content of at least 50 wt %. Furthermore, a content of at least 8 wt % of polystyrene is also always contained as the second polymer substance B. The specified content between 8 wt % and 40 wt %, preferably between 10 wt % and 20 wt %, has been found to be advantageous for strengthening and stiffening the asymmetric styrene-diene triblock copolymer, which in itself is very easy to stretch, without excessively impairing the elastic properties. Furthermore, it must be noted that polystyrene as polymer substance B is more economical than the asymmetric styrene-diene triblock copolymer, and therefore the use of polystyrene results in cost savings. This applies particularly in comparison to the design of a monofilm known from EP 2 264 101, in which two styrene-diene triblock copolymers are mixed with each other.

The ratio of polymer substance A to polymer substance B is preferably in a range between 3:1 and 6:1.

The monofilm is preferably formed by cast film extrusion, and the polymer mixture is extruded through an extrusion slit of a slit die by an extruder.

With a suitable mixture of polymer substance A and polymer substance B, a microphase-separated structure having stiffened domains oriented in a production direction can be produced in the monofilm. Individual stiffened domains formed substantially by polymer substance B and the terminal blocks of polymer substance A can be cylindrical or filament-shaped, for example. Such cylindrical or filament-shaped domains extending in the production direction, impart a comparatively high tensile strength in the production direction, as a result of which the monofilm can be well processed. However, the domains have only comparatively little effect transversely, and therefore the elastic monofilm remains easy to stretch transversely in direction (CD). This therefore achieves the advantage of a pronounced asymmetry of the stretch behavior, which asymmetry is desired in the context of the invention.

In order to be able to change the mechanical properties of the monofilm, the processability, the color, the UV stability, or further specific properties of the monofilm, at least one additional constituent, selected from the group of polyethylene (PE), ethylene vinyl acetate (EVA) antiblocking agents, pigments, thermal stabilizers, UV absorbers, and processing aids, can be present in addition to the first polymer substance A and the second polymer substance B.

Polymer substance A, i.e. preferably a styrene-isoprene-styrene block copolymer as an asymmetric styrene-diene triblock copolymer, preferably has a melt flow index MFI 200° C./5 kg as per ISO 1133 between 10 and 50.

The elastic monofilm can be used in particular to economically produce a laminate for a disposable hygiene product. The monofilm can be laminated against a nonwoven material, for example, and can then optionally be activated transversely (CD) depending on the type of lamination and the mechanical properties of the nonwoven material. In the case of activation, the laminate is stretched, for example by ring rollers or a stretching frame, and then relaxed, before first use. However, depending on the embodiment, such activation can be dispensed with, in particular if the nonwoven material is sufficiently easy to stretch without activation of the laminate.

Further subject matter of the invention is a method of making a laminate for disposable hygiene products, in particular for a diaper, the laminate including an elastic monofilm and at least one cover layer of nonwoven material, wherein a polymer mixture is plasticized in an extruder and comprises at least an asymmetric styrene-diene triblock copolymer at a content between 30 wt % and 90 wt % as a first polymer substance A and polystyrene at a content between 8 wt % and 40 wt % as a second polymer substance B, the polymer mixture then being extruded through a slit die in order to form a monofilm that is laminated with at least one nonwoven-material layer.

The laminate is preferably cut and applied to the diaper in such a way that the formed section can be stretched transversely with respect to the production direction of the monofilm. The elastic laminate can be used, for example, to form elastic diaper ears, elastic closure strips for a hook-and-loop fastener, or elastic side parts of a training diaper.

In the method, the laminate is optionally activated before installation in the diaper.

The mechanical properties in the case of a mixture of polystyrene with a symmetric styrene-diene triblock copolymer differ significantly from the mechanical properties in the case of the mixture of styrene with an asymmetric styrene-diene triblock copolymer, and therefore the mechanical properties resulting for the design of the monofilm according to the invention are surprising.

BRIEF DESCRIPTION OF THE DRAWING

Below, the invention is explained further with reference to a drawing in which.

SPECIFIC DESCRIPTION OF THE INVENTION

Figure 1:
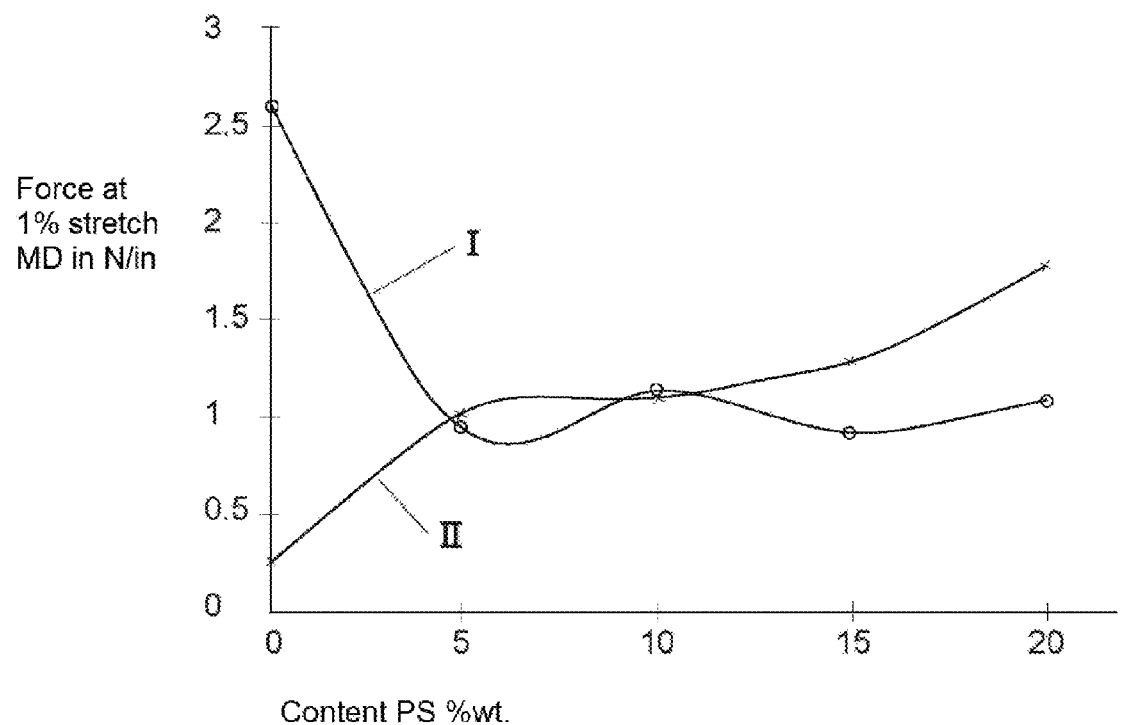
FIG. 1 shows a comparison of the force necessary for a stretch of 1% for different monofilms.

In FIG. 1, the force for 1% stretch of a monofilm in dependence on the content of polystyrene as polymer substance B in wt % is indicated in relative units. Curve I shows the curve of a monofilm not comprised by the invention that is formed from a mixture of a symmetric styrene-isoprene-styrene block copolymer and polystyrene. A certain amount of polystyrene is necessary to improve the flowability of the mixture. In addition, the raw-material costs of the mixture generally decrease with an increasing content of polystyrene. With the addition of polystyrene, the stiffness decreases at first and then remains relatively stable from a content of approximately 6 wt %.

In contrast, curve II shows the stretch behavior of a monofilm formed from an asymmetric styrene-isoprene-styrene block copolymer and polystyrene. The monofilm thus formed initially has a significantly lower stiffness that, however, continuously rises as polystyrene is added. At a content of at least 10 wt % of polystyrene, a higher level than that of curve I is achieved, despite an initially lower starting stiffness.

Figure 2A:
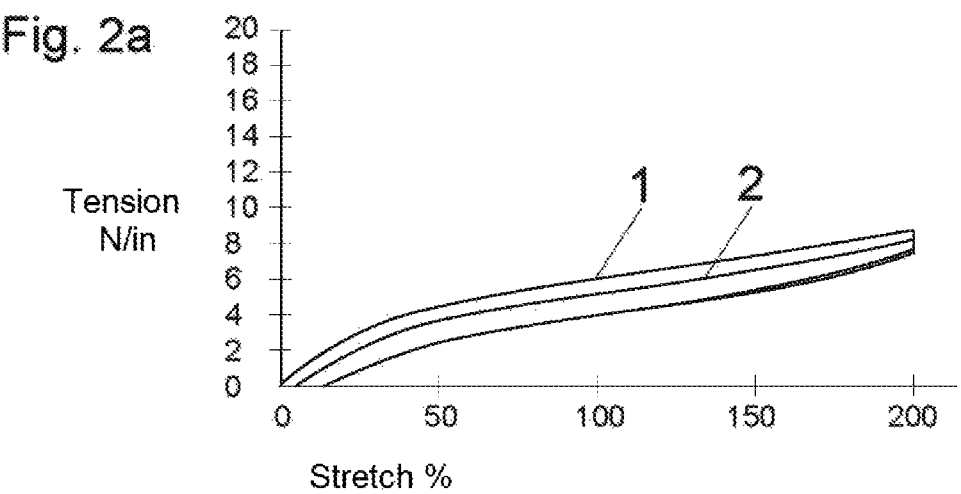
FIGS. 2a to 3c are stretch graphs for different monofilms.
Figure 2B:
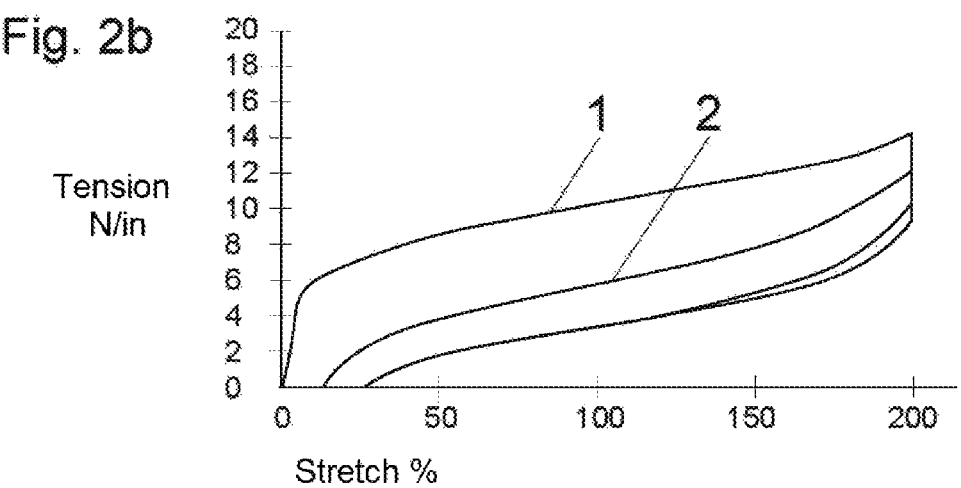
Figure 2C:
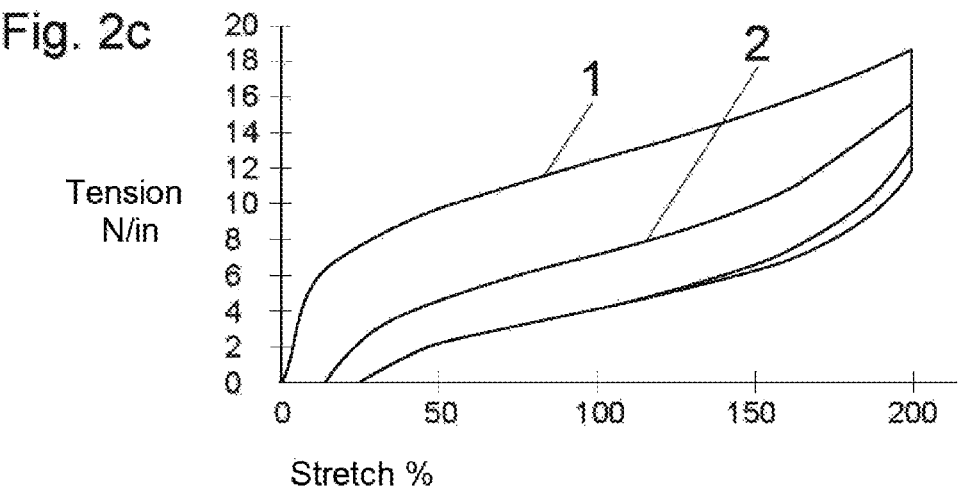

FIGS. 2a to 2c show, in relative units, the stretch behavior of a monofilm formed on the basis of asymmetric styrene-isoprene-styrene block copolymer for stretch in the machine direction (MD). FIG. 2a shows the stretch behavior for a polystyrene content of 0%, and therefore FIG. 2a concerns a comparison example.

According to FIG. 2a, a monofilm comprising an asymmetric styrene-isoprene-styrene block copolymer without any polystyrene has only low stiffness in the machine direction and thus cannot be processed or can be processed only with considerable complexity. The stretch graph shows the typical curve for a first-time stretch 1 and a subsequent second stretch 2, in each case with subsequent relaxation of the monofilm.

FIGS. 2b and 2c show a design of the monofilm according to the invention comprising a content of polystyrene of 10 wt % (FIG. 2b) and 20 wt % (FIG. 2c). It can be seen that the film is significantly stiffer in the machine direction (MD) and thus also can be well processed.

Figure 3A:
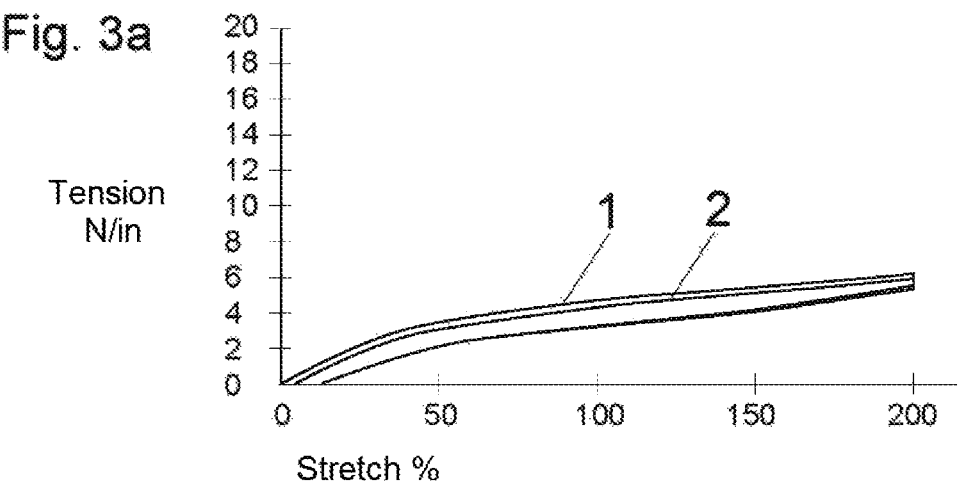
Figure 3B:
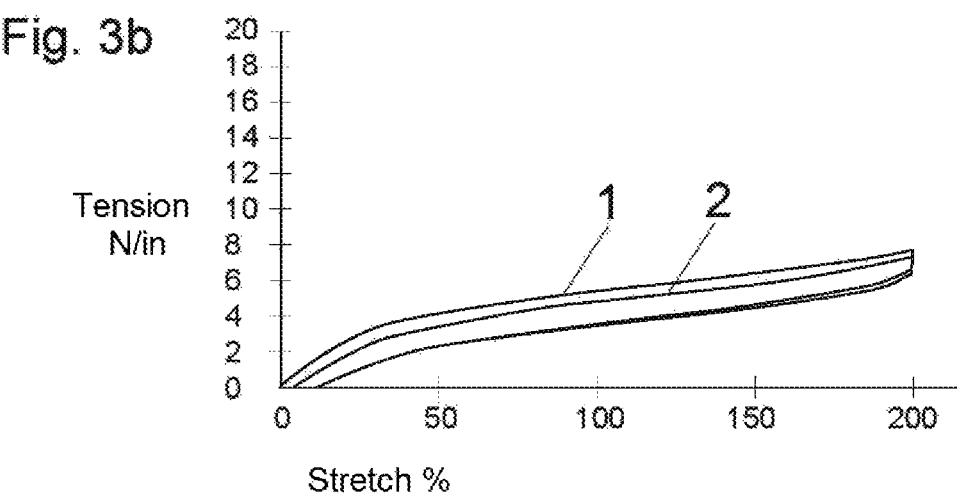
Figure 3C:
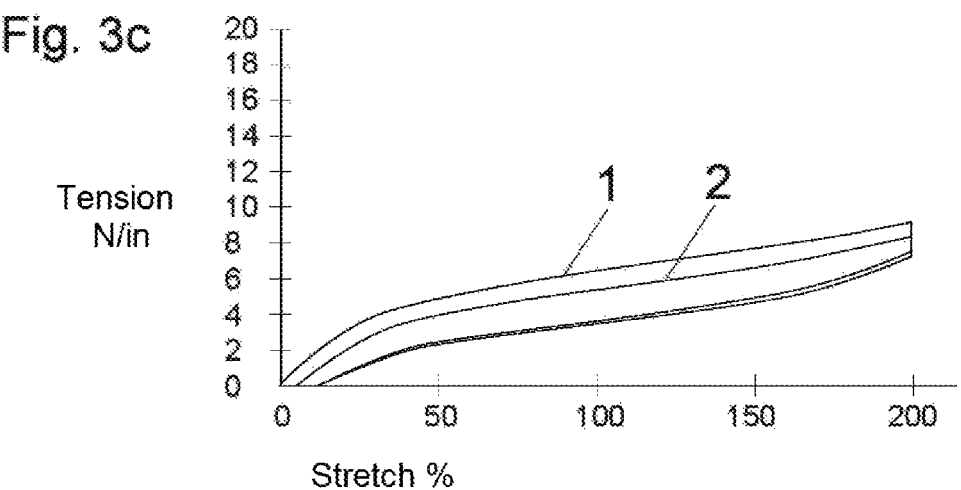

FIGS. 3a to 3c show the stretch behavior of the monofilm transversely (CD) in the same order. For the comparison example according to FIG. 3a having a polystyrene content of 0 wt %, an asymmetric behavior of the monofilm that is only slightly pronounced overall results in comparison with FIG. 2a, the monofilm being easy to stretch in both the machine direction (MD) and the transverse direction (CD).

While the stiffness in the machine direction (MD) significantly rises with an increasing content of polystyrene according to FIGS. 2b and 2c, the tensile forces required transversely (CD) change only slightly. Only a slight increase results. The monofilm according to the invention has a pronounced asymmetry of the stretch behavior, and, on the one hand, tensile forces can be adequately absorbed in the machine direction (MD) while, on the other hand, the monofilm remains easy to stretch transversely (CD).

The elastic monofilm typically can be elongated by at least 100%, preferably by at least 200%, from an original length. When the film is relaxed after a first stretching, a plastic portion of the deformation remains, which is also referred to as permanent stretch or permanent set. The present invention relates in particular to elastic films that have a permanent stretch of less than 50% after a stretch of 100%. In general, the permanent stretch of the film according to the invention is significantly lower. Thus, for example, values of the permanent stretch of less than 10% and in particular less than 6% can be achieved for a stretch of 200%.

The invention claimed is:

1. An elastic monofilm having a film thickness between 20 μm and 100 μm, the monofilm consisting of:
   an asymmetric styrene-diene triblock copolymer at a content between 30 wt % and 90 wt % based on the weight of the monofilm as a first polymer and having terminal blocks with a mass ratio between 2:1 and 5:1;
   a second polymer of polystyrene at a content between 8 wt % and 40 wt % based on the weight of the monofilm; and
   remainder at least one additional constituent of polyethylene, an ethylene vinyl acetate blocking agent, a pigment, a thermal stabilizer, a UV absorber as a stabilizer, or a processing aid.

2. The elastic monofilm according to claim 1, wherein the second polymer is provided at a content between 10 wt % and 20 wt %.

3. The elastic monofilm according to claim 1, wherein the ratio of the first polymer to the second polymer lies between 3:1 and 6:1.

4. The elastic monofilm according to claim 1, wherein the elastic monofilm is formed by cast film extrusion and has a microphase-separated structure having stiffened domains oriented in a production direction.

5. The elastic monofilm according to claim 1, wherein the asymmetric styrene-diene triblock copolymer is a styrene-isoprene-styrene block copolymer.

* * * * *